(12) United States Patent
Motomura

(10) Patent No.: US 6,251,276 B1
(45) Date of Patent: Jun. 26, 2001

(54) LEUKOCYTE ELIMINATING FILTER AND METHOD FOR MANUFACTURING THE SAME

(75) Inventor: Tadahiro Motomura, Kanagawa (JP)

(73) Assignee: Terumo Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/475,025

(22) Filed: Dec. 30, 1999

(30) Foreign Application Priority Data

Jan. 7, 1999 (JP) .................................................. 11-001756

(51) Int. Cl.$^7$ .................................................. B01D 71/58
(52) U.S. Cl. .............................. 210/500.37; 210/500.35; 210/490; 264/48; 264/49; 427/244
(58) Field of Search ............................ 210/500.27, 500.1, 210/500.35, 500.37, 490; 264/48, 49; 427/244

(56) References Cited

U.S. PATENT DOCUMENTS

| | | |
|---|---|---|
| 2,723,256 | 11/1955 | Hayek . |
| 3,948,866 | 4/1976 | Pennewiss et al. . |
| 4,154,647 | * 5/1979 | Rave . |
| 4,663,222 | * 5/1987 | Ohue et al. . |
| 5,164,087 | * 11/1992 | Naoi et al. . |
| 5,498,336 | * 3/1996 | Katsurada et al. . |
| 5,547,576 | * 8/1996 | Onishi et al. . |

* cited by examiner

Primary Examiner—Ana Fortuna
(74) Attorney, Agent, or Firm—Burns, Doane, Swecker & Mathis, LLP

(57) ABSTRACT

There is provided a leukocyte eliminating filter capable of exhibiting an excellent performance of eliminating leukocyte and platelet, which can be obtained through a simple process comprising the steps of coating a substrate constituting the filter with a polymer having a chemical structure represented by any one of the following formulas (I) and (II), and heat-drying the coated polymer:

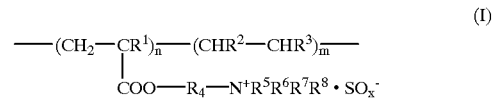

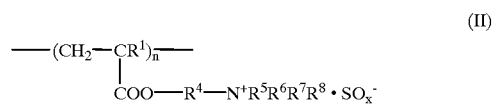

wherein $R^1$, $R^3$, $R^4$, $R^5 R^6$ and $R^7$ may be the same or different and are individually hydrogen atom or an alkyl group having 1 to 4 carbon atoms; $R^2$ is $CONH_2$ or $COOH$; $R^8$ is an alkyl group having 1 to 12 carbon atoms; and x is an integer of 3 or 4.

6 Claims, No Drawings

LEUKOCYTE ELIMINATING FILTER AND METHOD FOR MANUFACTURING THE SAME

BACKGROUND OF THE INVENTION

This invention relates to a leukocyte eliminating filter and a method for manufacturing the same. More particularly, this invention relates to a cationized and hydrophilized leukocyte eliminating filter which is made from a porous film, and to the manufacturing method of such a leukocyte eliminating filter, wherein the surface of the porous film is rendered to retain (through coating, for instance) a hydrophilic polymer comprising an alkylsulfate or alkylsulfonate of primary, secondary, tertiary or quaternary amine, thereby modifying the surface of the porous film so as to cationize and hydrophilize the leukocyte eliminating filter.

It is usually conducted, on the occasion of blood transfusion, to eliminate of inactivate leukocyte through a centrifugal separation, a radiation exposure or filtration for the purpose of preventing the generation of various side reactions that may be caused as a result of blood transfusion, such as the induction of GVHD (Graft Versus Host Disease) which may be brought about—mainly due to the presence of leukocyte, or for the purpose of preventing an infectious disease that may be caused by a virus-infected leukocyte. Among them, the elimination of leukocyte by means of filtration is widely adopted as it can be executed at patient's bedside because of the reasons that the method is simple and low in cost.

It is desired in the operation of eliminating leukocyte at patient's bedside to employ a leukocyte eliminating filter which is not only excellent in leukocyte eliminating capability but also capable of performing a smooth filtration. Such a leukocyte eliminating filter can be obtained by modifying the surface of the porous film constituting the leukocyte eliminating filter. This surface modification involves, in meaning, not only to render the surface to become easily adherable by leukocyte in addition to the adjustment of pore size of the porous film for the physical elimination of leukocyte, but also to render the surface to become hydrophilic.

To render the surface of the leukocyte eliminating filter to become easily adherable by leukocyte can be achieved by cationizing the surface thereof. Because, since the surface of cell such as leukocyte is electronegatively charged, it is known that, in order to eliminate the electronegative charge, the surface of the leukocyte eliminating filter is required to have positive electric charge (U.S. Pat. No. 3,242,073; and No. 3,352,424).

Further, when the surface of the leukocyte eliminating filter is rendered to be hydrophilic, blood is allowed to pass through the filter with little resistance at the moment when blood or blood preparation is contacted with the leukocyte eliminating filter, thereby making it possible to realize a smooth filtration thereof. As one of the indexes representing the hyrophilicity of the surface of filter, there is known a method of employing the critical wet surface tension thereof (hereinafter referred simply to as CWST, which will be explained below in detail).

BRIEF SUMMARY OF THE INVENTION

Therefore, an object of the present invention is to provide a leukocyte eliminating filter which can be easily manufactured and a method for manufacturing the filter, which can be realized through the cationization and hydrophilization of the surface of a substrate constituting the leukocyte eliminating filter for the purpose of improving the elimination of leukocyte.

It has been found as a result of intensive studies by the present inventors that the aforementioned objects can be realized by coating a leukocyte eliminating filter with a polymer having a chemical structure represented by any one of the following formulas (I) and (II), which are conventionally known as an antistatic agent, the coated polymer being subsequently heated to dry, thereby accomplishing this invention.

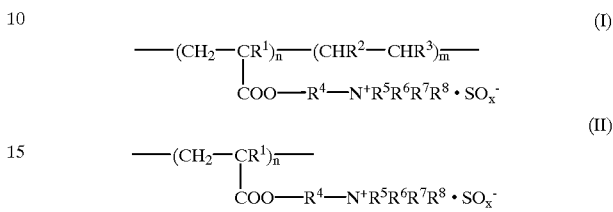

wherein $R^1$, $R^3$, $R^4$, $R^5$, $R^6$ and $R^7$ may be the same or different and are individually hydrogen atom or an alkyl group having 1 to 4 carbon atoms; $R^2$ is $CONH_2$ or $COOH$; $R^8$ is an alkyl group having 1 to 12 carbon atoms; and x is an integer of 3 or 4.

DETAILED DESCRIPTION OF THE INVENTION

This invention will be further explained as follows.

The porous substrate for the leukocyte eliminating filter may be a porous body, a plane film, a hollow fiber, an unwoven fabric, a woven fabric, or a composite thereof. The porosity of the substrate should preferably be in the range of 75% to 95%, more preferably in the range of 80% to 95%, and the pore diameter thereof as measured by means of the mercury injecting method should preferably be in the range of 0.1 to 30 $\mu$m, more preferably in the range of 2 to 20 maikuro $\mu$m. The reasons for limiting features of the substrate in these ranges are as follows. Namely, if the porosity of the substrate is 75% or more, it becomes possible to minimize the filtration time, while if the porosity of the substrate is 95% or less, it becomes possible to ensure the strength of the filter. On the other hand, if the pore diameter of the substrate is less than 0.1 $\mu$m, the clogging of the filter may be easily caused during the operation of eliminating leukocyte, thus making the filter useless, while if the pore diameter of the substrate is more than 30 $\mu$m, the frequency of contact between the blood or the leukocyte in blood preparation and the filter is deteriorated, thus reducing the trapping ratio of leukocyte.

In this description, $\mu$m means micro meter.

The leukocyte eliminating filter should preferably be constructed such that the substrate itself is cationic or the surface thereof is cationized. Because, since the cell surface of leukocyte is electronegatively charged, it would become easy to trap the leukocyte, if the surface of the leukocyte eliminating filter is made cationic.

As for the substrate constituting the leukocyte eliminating filter to be employed in this invention, it is possible to employ a fibrous body or a spongy body made from a natural polymer such as cotton and hemp; a synthetic polymer such as polyester (such as PET), polyacrylonitrile, polyolefin, polyolefin halide, polyurethane, polysulfone, polyether sulfone, poly(metha)acrylate, ethylene-polyvinyl alcohol copolymer, butadiene-acrylonitrile copolymer, etc.; or a mixture thereof. In view of the workability and the compatibility with blood however, a spongy polyurethane porous body is most preferable.

However, since these substrates for the blood filter, which are represented by polyurethane for instance, are generally highly hydrophobic in nature as they are, though they can be provided with an excellent leukocyte eliminating property due to their excellent workability and blood compatibility as mentioned above, it is rather difficult for blood to smoothly pass through the pores of the fibrous or spongy body thereof, so that some sort of hydrophilization treatment of these substrates is required to be performed.

If, in this case, the hydrophilization treatment thereof can be conducted simultaneous with the cationization treatment thereof, these treatments can be accomplished once for all, thus making it possible to simplify the working process and to improve the production efficiency. According to this invention, it is now possible, through a simple operation, to improve the hydrophilicity of the substrate, and at the same time, to promote the leukocyte eliminating performance of the substrate, thus increasing the production capacity of the filter.

Followings are specific examples of coating agent to be suitably employed in this invention.

Discussing more specifically, the coating agents to be suitably employed in this invention are high molecular compounds which can be represented by the following general formulas (I) and (II).

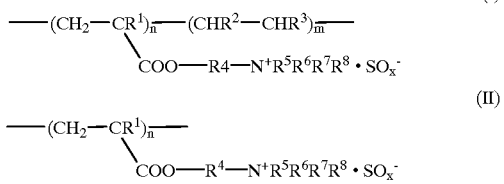

wherein $R^1$, $R^3$, $R^4$, $R^5$, $R^6$ and $R^7$ may be the same or different and are individually hydrogen atom or an alkyl group having 1 to 4 carbon atoms; $R^2$ is $CONH_2$ or COOH; $R^8$ is an alkyl group having 1 to 12 carbon atoms; and x is an integer of 3 or 4.

By the way, polymers represented by the aforementioned general formulas (I) and (II) where an alkylsulfate ion or an alkylsulfonate ion is employed as a counter ion can be synthesized by employing the methods set forth in U.S. Pat. No. 2,723,256 for instance, or are available since they are marketed as an antistatic agent. It is also possible to employ any other known techniques for the manufacture of these polymers represented by the aforementioned general formulas (I) and (II).

The ratio between n and m in the general formula (I) should preferably be in the range of 99:1 to 90:10 (n:m).

The molecular weight of the polymers represented by the aforementioned general formulas (I) and (II) should preferably be in the range of 650,000 to 1,050,000, more preferably in the range of 750,000 to 950,000. Because, if the molecular weight is limited within this range, the eluation of the polymer can be minimized.

As for the method of retaining these compounds on the porous film constituting the leukocyte eliminating filter, i.e. the method for manufacturing the leukocyte eliminating filter of this invention, it can be performed by a simple process wherein any one of the aforementioned coating agents is coated on the porous film by means of coating, dipping, spray or spin-coating, and then, the coated layer is heat-dried at a temperature of 60 to 100° C. It may be more preferable to perform the washing of the coated layer after the aforementioned heat-drying step so as to wash out any eluted matters.

Alternatively, it is also possible to employ a process wherein a quaternary amine ester of polyacrylic acid or of a copolymer of acrylic acid with acrylamide is coated on the substrate of the leukocyte eliminating filter, and then, the coated layer is heat-dried, the resultant dried layer being subsequently treated with an aqueous solution of sodium alkylsulfonate, or with an aqueous solution of sodium alkylsulfate.

By the way, the CWST, i.e. one of the indexes representing the hyrophilicity of the leukocyte eliminating filter of this invention is a value which can be determined by the following method which is set forth in EP 397403.

Namely, a plurality of aqueous solutions of calcium hydroxide, sodium hydroxide, calcium chloride, sodium nitrate, acetic acid, ethanol, etc. which are varied in concentration in such a manner that the surface tensions thereof are varied by 2 to 4 dyn/cm are prepared at first. Then, these aqueous solutions varied in surface tension by 2 to 4 dyn/cm are successively allowed to drop in order of surface tension (starting from the lowest one) and 10 drops by 10 drops on the surface of a leukocyte eliminating filter. These drops of aqueous solutions are then left to stand for 10 minutes. When it is possible that not less than nine drops out 10 drops could be absorbed by the leukocyte eliminating filter after the aforementioned 10-minute standing, the solution is determined as being a wet state, while when it is possible that less than nine drops out 10 drops could be absorbed by the leukocyte eliminating filter after the aforementioned 10-minute standing, the solution is determined as being a non-wet state. When the measurement is continued in order of surface tension starting from that of the lowest surface tension, the wet state as well as the non-wet state could be observed on the surface of the leukocyte eliminating filter. On this occasion, an average value of these values of surface tension of the aqueous solution where the wet state could be observed and of surface tension of the aqueous solution where the non-wet state could be observed is defined as being the value of CWST of the surface of the leukocyte eliminating filter. For example, if the wet state could be observed with the solution having a surface tension of 64 dyn/cm, and if non-wet state could be observed with the solution having a surface tension of 66 dyn/cm, the value of CWST of the surface of that leukocyte eliminating filter is determined as being 65 dyn/cm.

The value of CWST of the surface of the leukocyte eliminating filter according to this invention should preferably be in the range of 90 to 95 dyn/cm. Because, even if the value of CWST exceeds over 95 dyn/cm, there could not be recognized any substantial improvement on the penetration of blood (a substantial effect to be expected in this case) into the filter. On the other hand, if the value of this CWST is not less than 90 dyn/cm, a high penetration speed of blood could be expected, so that the operation of priming would not be required to be performed in advance and at the same time, the time required for the filtration can be shortened.

EXAMPLES

Nest, this invention will be explained with reference to the following examples, which are not intended to restrict the scope of this invention.

The measurement of the CWST in the following Examples and Comparative Examples was conducted in the same manner as explained above.

The measurements on the leukocyte eliminating ratio and the recovering ratio of platelet were performed as follow. Namely, the porous film which has been cationized and hydrophilized was punched to obtain a piece of porous film having a diameter of 25 mm, which was then attached to a module having an inlet port and an outlet port to obtain a leukocyte eliminating filter. On the other hand, a CPD-added fresh blood collected from a healthy volunteer was adjusted to prepare a concentrated solution of erythrocyte. Then, 5 mL of this concentrated solution of erythrocyte was allowed to flow down to the leukocyte eliminating filter from a level which is 10 cm higher than the leukocyte eliminating filter, and the quantities of leukocyte and blood plasma before and after the passing of the concentrated solution of erythrocyte through the leukocyte eliminating filter were measured. Based on the measured results, the elimination ratios of leukocyte and platelet were determined from the following formulas.

Leukocyte eliminating ratio=(1−(number of leukocyte after filtration/number of leukocyte before filtration))×100
Platelet eliminating ratio=(1−(number of platelet after filtration/number of platelet before filtration))×100

By the way, the number of leukocyte as well as the number of platelet were determined by making use of an automatic blood corpuscle measuring apparatus (SYSMEX E-9000(tradename); Toua Iryou Denshi Co., Ltd.).

Example 1

As a substrate for the leukocyte eliminating filter, a spongy polyurethane porous film (Rubycell; Toyo Polymer Co., Ltd.) 5.2 microns in average pore diameter, 86% in porosity and 1.2 mm in thickness was employed.

Then, this porous film was subjected to ultrasonic cleaning in hexane for one hour, and after being dried, dipped in an aqueous solution (0.3 w/w %) of a compound represented by the following formula (1): polyacrylamide-poly (acryloyloxy) ethyidiethylmethyl ammonium methylsulfonate (Calgon K400, tradename; Calgon Co., Ltd. ). Subsequently, the porous film was taken out of the aqueous solution and heat-treated for two hours at a temperature of 80° C., after which the porous film was shower-washed for four hours at room temperature and then, allowed to dry.

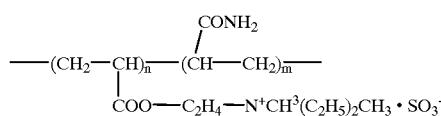

(1)

Thereafter, the leukocyte eliminating ratio and the platelet eliminating ratio were respectively determined according to the aforementioned process and by making use of the porous film prepared as explained above. In this case, the time interval between the initiation of flowing the blood and the initiation of oozing of the blood from the bottom surface (filtrate side) of the porous film after the porous film was completely filled with the blood (or wetting time) was also measured as a criterion for the hydrophilicity of the porous film. Then, the CWST of the porous film prepared as explained above was also measured according to the aforementioned method.

The results obtained are shown in Table 1 and Table 2.

Additionally, the elution tests of the porous film prepared as explained above were also performed to confirm the safety of the porous film. Namely, the elution tests of the porous film on the following five items were performed according to the specification standard for medical appliances and the standard for disposable transfusion sets and blood sets (Notice No.301 from the Ministry of Health and Welfare of Japan, 1970) ((1): External appearance; (2): pH; (3): potassium permanganate-reducing substances; (4): residues on evaporation; (5): heavy metals). It was confirmed as a result of these analyses that the porous film was capable of meeting these standards on all of the aforementioned items.

Example 2

The porous film obtained in Example 1 was subjected to ultrasonic cleaning in hexane for one hour, and after being dried, dipped in an aqueous solution (0.3 w/w %) of a compound represented by the following formula (2): polyacrylate-poly2-(acryloyloxy) ethyldiethylmethyl ammonium methylsulfate (Eletat U52, tradename; Ippousha Yushi Manufacturing Co., Ltd.).

Subsequently, the porous film was taken out of the aqueous solution and heat-treated for two hours at a temperature of 80° C., after which the porous film was shower-washed for four hours at room temperature and then, allowed to dry.

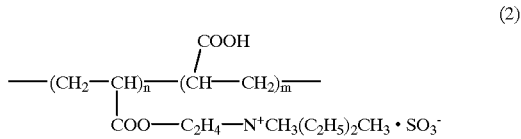

(2)

Thereafter, the leukocyte eliminating ratio and the platelet eliminating ratio were respectively determined according to the aforementioned process and by making use of the porous film prepared as explained above. In this case, the time interval between the initiation of flowing the blood and the initiation of oozing of the blood from the bottom surface (filtrate side) of the porous film after the porous film was completely filled with the blood (or wetting time) was also measured as a criterion for the hydrophilicity of the porous film. Then, the CWST of the porous film prepared as explained above was also measured according to the aforementioned method.

The results obtained are shown in Table 1 and Table 2.

Additionally, when the elution tests of the porous film prepared as explained in Example 1 were also performed to confirm the safety of the porous film, the porous film was confirmed as being capable of meeting these standards on all of the aforementioned items.

Example 3

The porous film obtained in Example 1 was subjected to ultrasonic cleaning in hexane for one hour, and after being dried, dipped in a 2-propanol solution (1 w/w %) of a compound represented by the following formula (3): poly (acryloyloxy) ethyldiethylmethyl ammonium methylsulfonate (Eletat U52, tradename; Ippousha Yushi Industries Co., Ltd. ).

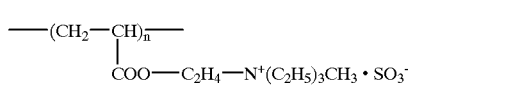

(3)

Subsequently, the porous film was taken out of the aqueous solution and heat-treated for two hours at a temperature of 80° C., after which the porous film was shower-washed for four hours at room temperature and then, allowed to dry.

Thereafter, the leukocyte eliminating ratio and the platelet eliminating ratio were respectively determined according to the aforementioned process and by making use of the porous film prepared as explained above. In this case, the time interval between the initiation of flowing the blood and the initiation of oozing of the blood from the bottom surface (filtrate side) of the porous film after the porous film was completely filled with the blood (or wetting time) was also measured as a criterion for the hydrophilicity of the porous film. Then, the CWST of the porous film prepared as explained above was also measured according to the aforementioned method.

The results obtained are shown in Table 1 and Table 2.

Additionally, when the elution tests of the porous film prepared as explained in Example 1 were also performed to confirm the safety of the porous film, the porous film was confirmed as being capable of meeting these standards on all of the aforementioned items.

Comparative Example 1

The same kind of polyurethane porous film as employed in Example 1 was subjected to ultrasonic cleaning in hexane for one hour, and then, allowed to dry.

Subsequently, by making use of this untreated porous film as a substrate for a leukocyte eliminating film, the leukocyte eliminating ratio and the platelet eliminating ratio were respectively determined according to the same procedures as explained in Example 1. In this case, the time interval between the initiation of flowing the blood and the initiation of oozing of the blood from the bottom surface (filtrate side) of the porous film after the porous film was completely filled with the blood (or wetting time) was also measured together with the CWST of the porous film.

The results obtained are shown in Table 1 and Table 2.

Comparative Example 2

Polyacrylamide-poly2-(acryloyloxy) ethyldiethylmethyl ammonium methylsulfate (Calgon K 400, tradename; Calgon Co., Ltd. ) was refined by allowing the polymer to repeatedly reprecipitate three times in tetrahydrofuran. This refined polymer was formulated into a 3 wt % aqueous solution thereof. Then, 50 mL of this aqueous solution was allowed to pass through Amberlite IRA 402BL Cl (Organo Co., Ltd.) which had been charged into a 50 mm×300 mm chromatographic column so as to allow the counter ion thereof to be exchanged with Cl—. Thereafter, the resultant compound was refined by repeatedly allowing it to reprecipitate three times in tetrahydrofuran, thereby synthesizing Calgon K 400 represented by the following formula (4) where the counter ion is constituted by Cl— ion.

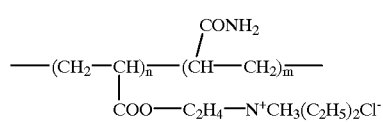
(4)

Then, the porous film of Example 1 was subjected to ultrasonic cleaning in hexane for one hour, and after being dried, dipped in an aqueous solution (0.3 w/w %) of Calgon K 400 represented by the following formula (4) where the counter ion is constituted by Cl— ion. Subsequently, the porous film was taken out of the aqueous solution and heat-treated for two hours at a temperature of 80° C., after which the porous film was shower-washed for four hours at room temperature and then, allowed to dry.

Thereafter, the leukocyte eliminating ratio and the platelet eliminating ratio were respectively determined according to the aforementioned process and by making use of the porous film prepared as explained above. In this case, the time interval between the initiation of flowing the blood and the initiation of oozing of the blood from the bottom surface (filtrate side) of the porous film after the porous film was completely filled with the blood (or wetting time) was also measured as a criterion for the hydrophilicity of the porous film.

The results obtained are shown in Table 1 and Table 2.

Example 4

The polymer obtained in Comparative Example 2 where the counter ion was constituted by Cl— ion was formulated into a 3 wt % aqueous solution thereof. Then, a 10 wt % aqueous solution of chlorine lauryl sulfate was added to 50 mL of this aqueous solution. As a result, since an insoluble polymer where the Cl ion was substituted by lauryl sulfate ion was gradually allowed to precipitate, the precipitated substance was recovered by means of filtration, thereby synthesizing Calgon K 400 represented by the following formula (5) where the counter ion is constituted by alkyl sulfate ion.

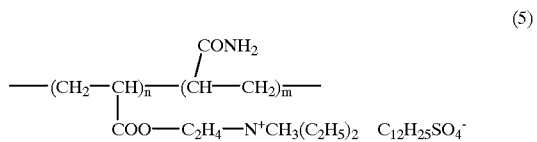
(5)

Then, the porous film of Example 1 was subjected to ultrasonic cleaning in hexane for one hour, and after being dried, dipped in an aqueous solution (0.3 w/w %) of Calgon K 400 represented by the following formula (5) where the counter ion was constituted by lauryl sulfate ion. Subsequently, the porous film was taken out of the aqueous solution and heat-treated for two hours at a temperature of 80° C., after which the porous film was shower-washed for four hours at room temperature and then, allowed to dry.

Thereafter, the leukocyte eliminating ratio and the platelet eliminating ratio were respectively determined according to the aforementioned process and by making use of the porous film prepared as explained above. In this case, the time interval between the initiation of flowing the blood and the initiation of oozing of the blood from the bottom surface (filtrate side) of the porous film after the porous film was completely filled with the blood (or wetting time) was also measured as a criterion for the hydrophilicity of the porous film.

The results obtained are shown in Table 1 and Table 2.

Example 5

A 30 g/m$^2$ of polyester unwoven fabric, which has 0.5 mm thickness and 30 μm in maximum pore diameter, and the unwoven fabric was made from fibers having a diameter of 1 to 5 μm (Tohnen Tapils Co., Ltd.) was dipped into a 3 w/w % aqueous coating solution of polyacrylamide-poly2-(acryloyloxy) ethyidiethylmethyl ammonium methylsulfate (Calgon K 400, tradename; Calgon Co., Ltd.). Then, the unwoven fabric was heat-dried for two hours at a temperature of 80° C., after which the unwoven fabric was shower-washed for four hours at room temperature to remove the substances eluted from the unwoven fabric, and then, allowed to dry.

Thereafter, the leukocyte eliminating ratio and the platelet eliminating ratio were respectively determined according to the aforementioned process and by making use of the unwoven fabric prepared as explained above.

The results obtained are shown in Table 1 and Table 2.

Comparative Example 3

A 30 g/m$^2$ of polyester unwoven fabric, which has 0.5 mm thickness and 30 μm in maximum pore diameter, and the unwoven fabric was made from fibers having a diameter of 1 to 5 μm (Tohnen Tapils Co., Ltd.) was shower-washed for four hours at room temperature to remove the substances eluted from the unwoven fabric, and then, allowed to dry.

Thereafter, the leukocyte eliminating ratio and the platelet eliminating ratio were respectively determined according to the aforementioned process and by making use of the unwoven fabric prepared as explained above.

The results obtained are shown in Table 1 and Table 2.

TABLE 1

| | CWST (dyn/cm) | Reflection absorbency | Leukocyte eliminated (%) | Platelet eliminated (%) |
|---|---|---|---|---|
| Ex. | | | | |
| 1 | 90 | 0.66 | 99.7 | 99.1 |
| 2 | 90 | 0.97 | 99.5 | 99.1 |
| 3 | 91 | 0.98 | 99.7 | 99.2 |
| 4 | 90 | 0.376 | 99.9 | 99.3 |
| 5 | — | 0.350 | 88.5 | 87.0 |
| C. Ex. | | | | |
| 1 | 72 | 0.03 | 87.0 | 21.2 |
| 2 | 72 | 0.124 | 87.8 | 21.8 |
| 3 | — | 0.06 | 61.0 | 35.0 |

TABLE 2

| | Wet time (sec.) |
|---|---|
| Example | |
| 1 | 11 |
| 2 | 25 |
| 3 | 13 |
| 4 | 20 |
| 5 | — |
| Comp. Example | |
| 1 | 41 |
| 2 | 40 |
| 3 | — |

Since the CWSTs of the leukocyte eliminating filters according to this invention represented by these examples were within the range of 90 to 95 dyn/cm as seen from the above results, the operation of priming by making use of physiological saline would not be required, and at the same time, the time required for the filtration of blood can be shortened, so that the time for emergency blood transfusion or the time for manufacturing a blood preparation can be shortened.

Additionally, since the leukocyte eliminating filters according to this invention represented by these examples were capable of exhibiting the excellent performance of eliminating leukocyte and platelet without necessitating a troublesome treatment of the filters, the manufacturing steps of the filters can be simplified, thus improving the productivity thereof.

Furthermore, since the leukocyte eliminating filters according to this invention represented by these examples were substantially free from any eluted matters, the filters can be safely employed as a leukocyte eliminating filter.

Namely, it is possible according to this invention to provide a leukocyte eliminating filter which is excellent in hydrophilicity and safety, and is capable of exhibiting the excellent performance of eliminating leukocyte and platelet, and which can be obtained through a simple manufacturing method comprising the steps of coating a polymer represented by the aforementioned formula (I) on a substrate constituting the leukocyte eliminating filter, heat-drying the coated substrate, and washing the dried substrate with water.

What is claimed is:

1. A leukocyte eliminating filter formed of a porous film, wherein the surface of said porous film is coated with at least one of polymers selected from the group consisting of polymers represented by any one of the following formulas (I) and (II):

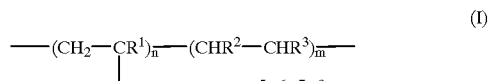

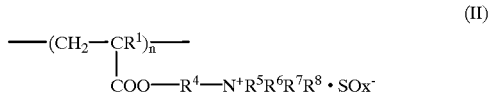

wherein $R^1$, $R^3$, $R^4$, $R^5$, $R^6$ and $R^7$ may be the same or different and are individually hydrogen atom or an alkyl group having 1 to 4 carbon atoms; $R^2$ is $CONH_2$ or $COOH$; $R^8$ is an alkyl group having 1 to 12 carbon atoms; and x is an integer of 3 or 4.

2. The leukocyte eliminating filter according to claim 1, wherein a critical wet surface tension of said filter is in the range of 90 to 95 dyn/cm.

3. The leukocyte eliminating filter according to claim 1, wherein said porous film is formed of a polyurethane porous body 0.1 to 30 μm in average pore diameter, and 75% to 95% in porosity.

4. A method of manufacturing a leukocyte eliminating filter formed of a porous film, which comprises the steps of:

coating a surface of said porous film with at least one of polymers selected from the group consisting of polymers represented by any one of the following formulas (I) and (II) to form a coated layer; and heat-drying said coated layer:

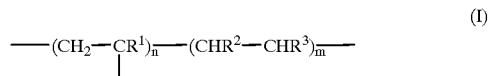

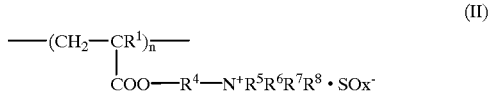

wherein $R^1$, $R^3$, $R^4$, $R^5$, $R^6$ and $R^7$ may be the same or different and are individually hydrogen atom or an alkyl group having 1 to 4 carbon atoms; $R^2$ is $CONH_2$ or $COOH$; $R^8$ is an alkyl group having 1 to 12 carbon atoms; and x is an integer of 3 or 4.

5. The method of manufacturing a leukocyte eliminating filter according to claim 4, wherein a critical wet surface tension of said filter is in the range of 90 to 95 dyn/cm.

6. The method of manufacturing a leukocyte eliminating filter according to claim 5, wherein said porous film is formed of a polyurethane porous body 0.1 to 30 μm in average pore diameter, and 75% to 95% in porosity.

* * * * *